(12) United States Patent
Xie et al.

(10) Patent No.: US 11,644,398 B1
(45) Date of Patent: May 9, 2023

(54) APPARATUS AND METHOD FOR TESTING COMBINED DYNAMIC-STATIC LOADING STRENGTH OF ROCK-LIKE MATERIAL

(71) Applicant: CHINA UNIVERSITY OF MINING AND TECHNOLOGY, Xuzhou (CN)

(72) Inventors: Lixiang Xie, Xuzhou (CN); Jiawan Jin, Xuzhou (CN); Chao Chen, Xuzhou (CN)

(73) Assignee: CHINA UNIVERSITY OF MINING AND TECHNOLOGY, Xuzhou (CN)

( * ) Notice: Subject to any disclaimer, the term of this patent is extended or adjusted under 35 U.S.C. 154(b) by 0 days.

(21) Appl. No.: 17/970,592

(22) Filed: Oct. 21, 2022

(30) Foreign Application Priority Data

Oct. 28, 2021 (CN) .......................... 202111259257.5

(51) Int. Cl.
*G01N 3/313* (2006.01)
*G01N 3/06* (2006.01)
*G01N 33/24* (2006.01)

(52) U.S. Cl.
CPC ............... *G01N 3/313* (2013.01); *G01N 3/06* (2013.01); *G01N 33/24* (2013.01); *G01N 2203/001* (2013.01); *G01N 2203/0026* (2013.01)

(58) Field of Classification Search
CPC .......... G01N 3/313; G01N 3/06; G01N 33/24; G01N 2203/001; G01N 2203/0026
USPC ........................................................... 73/794
See application file for complete search history.

(56) References Cited

U.S. PATENT DOCUMENTS

| | | |
|---|---|---|
| 11,016,010 B1 | 5/2021 | Li et al. |
| 2013/0002003 A1 | 1/2013 | Murray et al. |
| 2021/0325287 A1 | 10/2021 | Xie et al. |

FOREIGN PATENT DOCUMENTS

| | | | | |
|---|---|---|---|---|
| CN | 1731133 A | * | 2/2006 | |
| CN | 1731133 A | | 2/2006 | |
| CN | 103487337 A | | 1/2014 | |
| CN | 203616216 U | | 5/2014 | |
| CN | 104535409 A | * | 4/2015 | ............... G01N 3/00 |
| CN | 104931334 A | | 9/2015 | |
| CN | 105784976 A | | 7/2016 | |
| CN | 106226176 A | * | 12/2016 | ............. G01N 3/313 |
| CN | 106226176 A | | 12/2016 | |

(Continued)

OTHER PUBLICATIONS

Diyuan Li et al., Mechanical and failure properties of rocks with a cavity under coupled static and dynamic loads, Engineering Fracture mehanics, 225, Jun. 28, 2018 (Year: 2018).*

(Continued)

*Primary Examiner* — Marrit Eyassu
(74) *Attorney, Agent, or Firm* — Bayramoglu Law Offices LLC

(57) ABSTRACT

An apparatus and a method for testing combined dynamic-static loading strength of a rock-like material are provided. The apparatus and the method can test the combined dynamic-static loading strength of the rock-like material. The apparatus comprises an explosion load loading device, a static load loading device, and a stress wave rod transferring device. The explosion load loading device is connected with one end of the stress wave rod transferring device. The stress wave rod transferring device is connected with a rock-like material specimen. The stress wave rod transferring device is connected with the static load loading device.

8 Claims, 2 Drawing Sheets

(56) References Cited

FOREIGN PATENT DOCUMENTS

| | | | | |
|---|---|---|---|---|
| CN | 106932285 A | * | 7/2017 | |
| CN | 107314933 A | * | 11/2017 | ............... G01N 3/00 |
| CN | 108732047 A | | 11/2018 | |
| CN | 109490075 A | | 3/2019 | |
| CN | 109596666 A | | 4/2019 | |
| CN | 110082203 A | | 8/2019 | |
| CN | 110108551 A | | 8/2019 | |
| CN | 110108571 A | | 8/2019 | |
| CN | 110220794 A | | 9/2019 | |
| CN | 110672795 A | | 1/2020 | |
| CN | 111707431 A | | 9/2020 | |
| EP | 0855589 A1 | | 7/1998 | |
| KR | 101727405 B1 | | 5/2017 | |
| WO | 2019140874 A1 | | 7/2019 | |

OTHER PUBLICATIONS

D. S. Kim, et al., Quantitative Assessment of Extrinsic Damage in Rock Materials, Rock Mechanics and Rock Engineering, 1998, pp. 43-62, vol. 31, No. 1.

Xu Jinyu, et al., A study of the strength and deformability of underground rock under impact loadings, Protective Engineering, 2012, pp. 1-4, vol. 34, No. 6.

\* cited by examiner

APPARATUS AND METHOD FOR TESTING COMBINED DYNAMIC-STATIC LOADING STRENGTH OF ROCK-LIKE MATERIAL

CROSS REFERENCE TO THE RELATED APPLICATIONS

This application is based upon and claims priority to Chinese Patent Application No. 202111259257.5, filed on Oct. 28, 2021, the entire contents of which are incorporated herein by reference.

TECHNICAL FIELD

The present invention relates to the field of testing, and in particular, to an apparatus and a method for testing combined dynamic-static loading strength of a rock-like material.

BACKGROUND

In the prior art, the split-Hopkinson pressure rod can test the dynamic load strain and stress resistances of a rock impact load, and basically meets the requirements of engineering. However, explosives generate two destructive effects in a rock mass. The first is the effect of impact compression waves to the surrounding rock mass, and the second is the effect of gas expansion waves to the surrounding rock mass. The split-Hopkinson pressure rod mainly tests the first effect, so that the effect of the gas expansion waves to the surrounding rock mass is not considered. Meanwhile, the dynamic loading rate tested by the split-Hopkinson pressure rod is also limited.

SUMMARY

The present invention is intended to solve the technical problem by providing an apparatus and a method for testing combined dynamic-static loading strength of a rock-like material, which are used for testing the combined dynamic-static loading strength of the rock-like material.

To solve the technical problem, embodiments of the present invention adopt the following technical schemes:

In one aspect, embodiments of the present invention provide an apparatus for testing combined dynamic-static loading strength of a rock-like material, comprising an explosion load loading device, a static load loading device and a stress wave rod transferring device, wherein the explosion load loading device is connected with one end of the stress wave rod transferring device; the stress wave rod transferring device is connected with a rock-like material specimen; the stress wave rod transferring device is connected with the static load loading device.

Preferably, the explosion load loading device comprises a hole packer provided with a wire transferring hole, an explosion load loader, a rock-like material layer, a charging hole and a sealing cover, wherein: one end of the hole packer is fixedly connected with one end of the explosion load loader; an inner cavity of the explosion load loader is filled with the rock-like material layer; the charging hole is provided in the rock-like material layer; one end of the charging hole is communicated with the wire transferring hole; the charging hole is filled with an explosive; the sealing cover is fixedly connected with the other end of the explosion load loader.

Preferably, a wave-absorbing plate is provided on an inner wall of the explosion load loader.

Preferably, the stress wave rod transferring device comprises a solid incident rod and a transmission rod; one end of the solid incident rod passes through the sealing cover and is opposite to the charging hole; the other end of the solid incident rod is connected with the rock-like material specimen; one end of the transmission rod is connected with the rock-like material specimen; the solid incident rod and the transmission rod are positioned on two sides of the rock-like material specimen.

Preferably, a first end portion of the solid incident rod close to the charging hole is cylindrical; a truncated cone-shaped connecting portion is provided between the first end portion and a body of the solid incident rod; a diameter of the connecting portion gradually increases towards a direction of the charging hole.

Preferably, the transmission rod is a hollow rod or a solid rod.

Preferably, the static load loading device comprises a confining pressure loader, an axial pressure carrier and an axial pressure loader, wherein: the confining pressure loader comprises a front loader with a sound emission wire transferring hole, a rear loader with a sound emission wire transferring hole, an upper loader with a sound emission wire transferring hole, and a lower loader with a sound emission wire transferring hole; the front loader is positioned at a front portion of the rock-like material specimen; the rear loader is positioned at a rear portion of the rock-like material specimen; the upper loader is positioned at an upper portion of the rock-like material specimen; the lower loader is positioned at a lower portion of the rock-like material specimen; the sound emission wire transferring hole of the front loader, the sound emission wire transferring hole of the rear loader, the sound emission wire transferring hole of the upper loader and the sound emission wire transferring hole of the lower loader all face the rock-like material specimen; one end of the axial pressure carrier is connected with the transmission rod; and the axial pressure loader is connected with the other end of the axial pressure carrier.

In another aspect, embodiments of the present invention further provides a method for testing combined dynamic-static loading strength of a rock-like material, comprising:

S10, molding a filling material: connecting the hole packer with one end of the explosion load loader in a threaded manner, filling the explosion load loader with the rock-like material layer, and placing the T-shaped mold during the filling process;

S20, charging: after the rock-like material layer is molded, removing the T-shaped mold to form the charging hole and the port, mounting and binding an electronic detonator in the explosive, threading a leg wire connected to the electronic detonator through the wire transferring hole, and placing the explosive in the charging hole;

S30, connecting the devices: connecting the explosion load loader with the sealing cover; placing the first end portion of the solid incident rod into the port of an inner cavity of the rock-like material layer; sequentially connecting the rock-like material specimen with the solid incident rod, connecting the transmission rod with the rock-like material specimen, connecting the transmission rod with the axial pressure carrier, and connecting the axial pressure carrier with the axial pressure loader; placing the front loader at the front portion of the rock-like material specimen, placing the rear loader at the rear portion of the rock-like material specimen, placing the upper loader at the upper portion of the rock-like material specimen, and placing the lower loader at the lower portion of the rock-like material specimen; mounting a sound emission probe on the rock-like material specimen, and outputting wires of the sound emission probe through the sound emission wire transferring holes of the front loader, the rear loader, the upper loader and the lower loader; pasting super-dynamic strain gauges at middle portions of the solid incident rod and the transmission rod;

S40, loading a static load: applying an axial pressure load to the transmission rod through the axial pressure loader; sequentially transferring the pressure load to the rock-like material specimen, the solid incident rod and the rock-like material layer through the transmission rod, and compacting the rock-like material layer under the action of the pressure load; applying different lateral pressure loads to the rock-like material specimen through the front loader, the rear loader, the upper loader, and the lower loader of the confining pressure loader;

S50, loading a dynamic load: detonating the explosive in the charging hole through the leg wire in the wire transferring hole, wherein impact waves and gas expansion waves generated by the explosion of the explosive push the solid incident rod to act on the rock-like material specimen, such that the combined dynamic-static loading can be achieved on the rock-like material specimen; and S60, acquiring stress wave data: during the loading of the dynamic load, acquiring data in the super-dynamic strain gauges on the solid incident rod and the solid transmission rod.

Preferably, in step S10, the T-shaped mold and the wire transferring hole are coaxial; one end portion of the T-shaped mold has the same size as the first end portion of the solid incident rod; a body of the T-shaped mold has the same size as the charging hole; the charging hole is communicated with the wire transferring hole in the hole packer.

Preferably, in step S60, when the transmission rod is a hollow rod, a spalling strength is obtained by test; when the transmission rod is a solid rod, a dynamic stress resistance is obtained by test.

Compared with the prior art, the embodiments of the present invention have the following beneficial effects: according to the apparatus and the method for testing the combined dynamic-static loading strength of the rock-like material, after the impact waves and the gas expansion waves generated by the explosion of the explosive act on surrounding media, the intensive impact load generated may act on the rock-like material to test the combined dynamic-static loading strength of the rock-like material. Embodiments of the present invention consider the action factors of the impact waves and the gas expansion waves generated after the explosive explodes in a rock mass in the actual blasting engineering on the surrounding media. The specific implementation is that an explosive is buried in a dynamic load loading device; after the explosive in a rock-like material layer of the dynamic load loading device is detonated and explodes, impact waves and gas expansion waves are generated and act on the surrounding rock-like material media, and then push the solid incident rod to act on a rock-like material specimen, such that the rock-like material specimen is destroyed. In addition, the spalling strength of the rock-like material specimen is tested by utilizing the spalling damage to the rock mass caused by reflected tensile waves generated by mismatch of the wave impedance.

Figure 1:
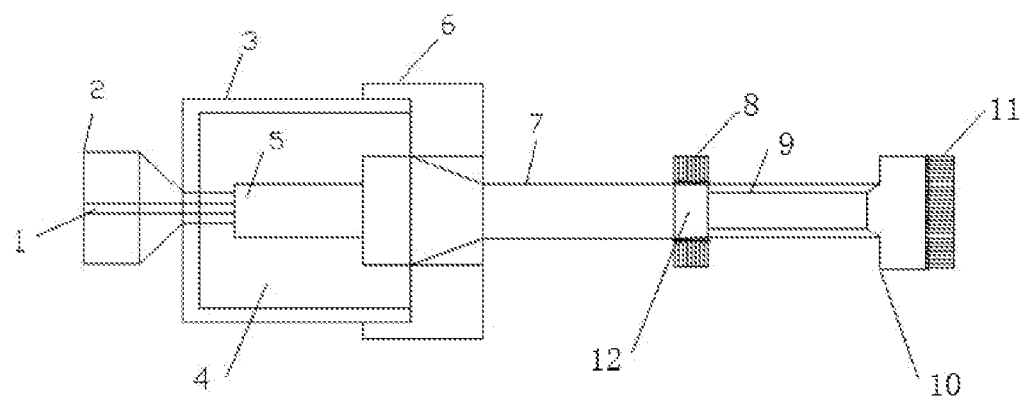
FIG. 1 is a schematic structural diagram according to embodiments of the present invention.
Figure 2:
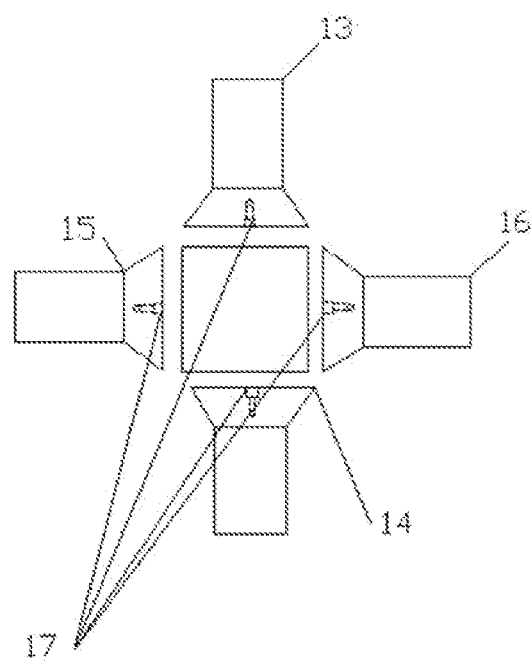
FIG. 2 is a schematic layout diagram of a confining pressure loader according to embodiments of the present invention.
Figure 3:
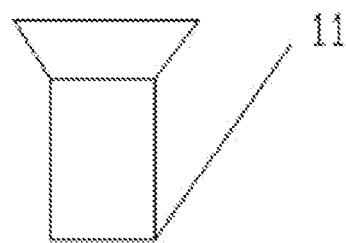
FIG. 3 is a schematic structural diagram of an axial pressure loader according to embodiments of the present invention.
Figure 4:
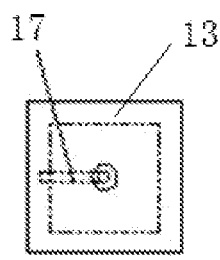
FIG. 4 is a front view of a front loader according to embodiments of the present invention.

In the drawings, the numerals represent the following features: wire transferring hole 1, hole packer 2, explosion load loader 3, rock-like material layer 4, charging hole 5, sealing cover 6, solid incident rod 7, confining pressure loader 8, transmission rod 9, axial pressure carrier 10, axial pressure loader 11, rock-like material specimen 12, front loader 13, rear loader 14, upper loader 15, lower loader 16, and sound emission wire transferring hole 17.

DETAILED DESCRIPTION OF THE EMBODIMENTS

The technical schemes of the present invention will be illustrated in detail below with reference to the attached drawings.

An apparatus for testing strength of a rock-like material according to embodiments of the present invention comprises an explosion load loading device, a static load loading device and a stress wave rod transferring device. The explosion load loading device is connected with one end of the stress wave rod transferring device; the stress wave rod transferring device is connected with a rock-like material specimen 12; the stress wave rod transferring device is connected with the static load loading device.

The dynamic loading to the rock-like material specimen 12 is achieved by providing the explosion load loading device and the stress wave rod transferring device. The static loading to the rock-like material specimen 12 is achieved by providing the static load loading device and the stress wave rod transferring device. Strength data are acquired through the stress wave rod transferring device. According to the embodiment, the strength data of the rock-like material specimen 12 can be acquired in a condition that dynamic loading and static loading are simultaneously loaded to the rock-like material specimen 12. According to the embodiment, after the impact waves and the gas expansion waves generated by the explosion of the explosive act on surrounding media, the intensive impact load generated may act on the rock-like material to test the combined dynamic-static loading strength of the rock-like material.

Preferably, as shown in FIG. 1, the explosion load loading device comprises a hole packer 2 provided with a wire transferring hole 1, an explosion load loader 3, a rock-like material layer 4, a charging hole 5 and a sealing cover 6. One end of the hole packer 2 is fixedly connected with one end of the explosion load loader 3; an inner cavity of the explosion load loader 3 is filled with the rock-like material layer 4; the charging hole 5 is provided in the rock-like material layer 4; one end of the charging hole 5 is communicated with the wire transferring hole 1; the charging hole 5 is filled with an explosive. The sealing cover 6 is fixedly connected with the other end of the explosion load loader 3. The hole packer 2 is hermetically connected with the explosion load loader 3. The sealing cover 6 is hermetically connected with the explosion load loader 3. A space is formed among the hole packer 2, the explosion load loader 3 and the sealing cover 6. The space is filled with the rock-like material layer 4. The rock-like material layer 4 is used for simulating the effects of impact waves and gas expansion waves generated after the explosive explodes in a rock mass, and then the solid incident rod 7 is pushed to act on the rock-like material specimen 12. The charging hole 5 is provided in the rock-like material layer 4, and is filled with the explosive. The wire transferring hole 1 of the hole packer 2 is used for outputting a leg wire of the explosive. The explosion load loading device is used for applying dynamic loading to the rock-like material specimen 12.

The interior of the rock-like material layer 4 is machined into a T shape before the explosive is placed, and a lower portion of the T shape is used for placing the explosive. An upper portion of the T shape matches a convex end portion of the solid incident rod in size, and the hole packer 2 and the sealing cover 6 cover the exterior of the rock-like material layer 4. Such a structure is used for preventing gas from leaking out after the explosive explodes. In addition, the dynamic load is directly in contact with the end portion of the solid incident rod 7 after the explosive explodes. The structure can maintain a contact area between the dynamic load and the solid incident rod 7 after the explosive explodes, which is beneficial to providing higher energy acting on the solid incident rod 7, leading to a higher loading strength that impacts the rock-like material specimen 12.

Preferably, a wave-absorbing plate is provided on an inner wall of the explosion load loader 3. Providing the wave-absorbing plate can eliminate the influence of stress wave reflection on the impact waves and the expansion waves in the loading process. The wave-absorbing plate is adopted to eliminate the influence of waves reflected by the inner wall on the dynamic load. The wave-absorbing plate is provided with holes on a surface to absorb waves in a contact interface.

Preferably, as shown in FIG. 1, the stress wave rod transferring device comprises a solid incident rod 7 and a transmission rod 9.

One end of the solid incident rod 7 passes through the sealing cover 6 and is opposite to the charging hole 5. The other end of the solid incident rod 7 is connected with the rock-like material specimen 12; one end of the transmission rod 9 is connected with the rock-like material specimen 12; the solid incident rod 7 and the transmission rod 9 are positioned on two sides of the rock-like material specimen 12. The function of the solid incident rod 7 is to provide a stress wave input end for the rock-like material specimen 12. The function of the transmission rod 9 is to provide a stress wave output end. When the transmission rod 9 is a hollow rod, a strain spalling resistance of the rock-like material specimen 12 can be tested. When the transmission rod 9 is a solid rod, a stress resistance of the rock-like material specimen 12 can be tested.

Preferably, a first end portion of the solid incident rod 7 close to the charging hole 5 is cylindrical; a truncated cone-shaped connecting portion is provided between the first end portion and a body of the solid incident rod 7; a diameter of the connecting portion gradually increases towards a direction of the charging hole 5. A transitional connecting portion is provided between the first end portion of the solid incident rod 7 and the body of the solid incident rod 7, and a diameter of the connecting portion gradually changes. The first end portion of the solid incident rod 7 is cylindrical and has a truncated cone-shaped transitional connecting portion to play a role of waveform shaping.

Preferably, as shown in FIG. 1 to FIG. 4, the static load loading device comprises a confining pressure loader 8, an axial pressure carrier 10 and an axial pressure loader 11. The confining pressure loader 8 comprises a front loader 13 with a sound emission wire transferring hole 17, a rear loader 14 with a sound emission wire transferring hole 17, an upper loader 15 with a sound emission wire transferring hole 17, and a lower loader 16 with a sound emission wire transferring hole 17; the front loader 13 is positioned at a front portion of the rock-like material specimen 12; the rear loader 14 is positioned at a rear portion of the rock-like material specimen 12; the upper loader 15 is positioned at an upper portion of the rock-like material specimen 12; the lower loader 16 is positioned at a lower portion of the rock-like material specimen 12; the sound emission wire transferring hole 17 of the front loader 13, the sound emission wire transferring hole 17 of the rear loader 14, the sound emission wire transferring hole 17 of the upper loader 15 and the sound emission wire transferring hole 17 of the lower loader 16 all face the rock-like material specimen 12. One end of the axial pressure carrier 10 is connected with the transmission rod 9; and the axial pressure loader 11 is connected with the other end of the axial pressure carrier 10. The front loader 13, the rear loader 14, the upper loader 15 and the lower loader 16 provide confining pressures in different directions towards the rock-like material specimen 12. An axial pressure is provided for the axial pressure carrier 10 by the axial pressure loader 11. The transmission rod 9 applies a pressure to the rock-like material specimen 12, so as to apply an axial pressure to the rock-like material specimen 12. The front loader 13, the rear loader 14, the upper loader 15, and the lower loader 16 are provided with the sound emission wire transferring holes 17. A portion of each sound emission wire transferring hole 17 that is in contact with the rock-like material specimen 12 is provided with a large groove. After a sound emission probe is mounted on the rock-like material specimen 12, a protruding portion of the sound emission probe is placed at the groove portion of the sound emission wire transferring hole 17. An output signal wire of the sound emission probe is output by a narrow hole of the sound emission wire transferring hole 17. Therefore, the sound emission wire transferring hole 17 has two functions: one is to accommodate the protruding portion of the sound emission probe and the other is wiring. The larger groove portion is used for accommodating the protruding portion of the sound emission probe, and the smaller groove portion is used for wiring. The sound emission probe is used for testing an emission rule of the sound generated by the rock-like material specimen 12 in a destroying process.

Also provided is a method of the apparatus for testing the strength of the rock-like material according to the above embodiments, comprising:

S10, molding of a filling material: the hole packer 2 with one end of the explosion load loader 3 are connected in a threaded manner, the explosion load loader 3 is filled with the rock-like material layer 4, and the T-shaped mold is placed during the filling process. The T-shaped mold is mainly used for providing the charging hole 5 and the port. The port is used for accommodating the first end portion of the solid incident rod 7.

S20, charging: after the rock-like material layer 4 is molded, the T-shaped mold is removed to form the charging hole 5 and the port, an electronic detonator is mounted and bound in the explosive, a leg wire connected to the electronic detonator is threaded through the wire transferring hole 1, and the explosive is placed in the charging hole 5.

S30, connection of the devices: the explosion load loader 3 is connected with the sealing cover 6; the first end portion of the solid incident rod 7 is placed into the port of an inner cavity of the rock-like material layer 4; the rock-like material specimen 12 is connected with the solid incident rod 7, the transmission rod 9 is connected with the rock-like material specimen 12, the transmission rod 9 is connected with the axial pressure carrier 10, and the axial pressure carrier 10 is connected with the axial pressure loader 11; the front loader 13 is placed at the front portion of the rock-like material specimen 12, the rear loader 14 is placed at the rear portion of the rock-like material specimen 12, the upper loader 15 is placed at the upper portion of the rock-like material specimen 12, and the lower loader 16 is placed at the lower portion of the rock-like material specimen 12; a sound emission probe is mounted on the rock-like material specimen 12, wires of the sound emission probe are output through the sound emission wire transferring holes 17 of the front loader 13, the rear loader 14, the upper loader 15 and the lower loader 16. Super-dynamic strain gauges are pasted at middle portions of the solid incident rod 7 and the transmission rod 9. The super-dynamic strain gauges are used for testing stress waves propagating in the solid incident rod 7 and the transmission rod 9. The sound emission probe acquires sound emission signals according to the emission rule of the sound generated by the rock-like material specimen 12 in a destroying process. Specifically, the sound emission signals acquired by the sound emission probe are transmitted and output to different directions through the sound emission wire transferring holes 17 of the front loader 13, the rear loader 14, the upper loader 15 and the lower loader 16, such that the emission rule of the sound generated by combined dynamic-static loading destruction of the rock-like material specimen is acquired.

S40, loading of a static load: an axial pressure load is applied to the transmission rod 9 through the axial pressure loader 11; the pressure load is sequentially transferred to the rock-like material specimen 12, the solid incident rod 7 and the rock-like material layer 4 through the transmission rod 9, and the rock-like material layer 4 is compacted under the action of the pressure load. In this process, an axial static load is applied to the rock-like material specimen 12. Different lateral pressure loads are applied to the rock-like material specimen 12 through the front loader 13, the rear loader 14, the upper loader 15, and the lower loader 16 of the confining pressure loader 8.

S50, loading of a dynamic load: the explosive in the charging hole (5) is detonated through the leg wire in the wire transferring hole (1), impact waves and gas expansion waves generated by the explosion of the explosive push the solid incident rod (7) to act on the rock-like material specimen (12), such that the combined dynamic-static loading can be achieved on the rock-like material specimen (12); and The solid incident rod 7 is used for generating a higher impact load acting on the rock-like material specimen 12 on one hand, and generating one-dimensional planar stress waves acting on the rock-like material specimen 12 on the other hand. If the solid incident rod 7 is hollow, the impact load is only transmitted to part of the rock-like material specimen 12. The stress resistance and the spalling strength of the combined dynamic-static loading may not be obtained if the planar stress waves do not act on the rock-like material 12.

S60, acquisition of stress wave data: during the loading of the dynamic load, data in the super-dynamic strain gauges on the solid incident rod 7 and the solid transmission rod 9 are acquired; a stress-strain curve is obtained through Formula (1) and Formula (2) after incident wave, transmitted wave and reflected wave signals are obtained, wherein the peak value of the stress-strain curve is the strength value.

$$\varepsilon = \frac{C_1}{L}\int_0^t (\varepsilon_I - \varepsilon_R)dt' - \frac{C_2}{L}\int_0^t \varepsilon_T dt' \quad \text{Formula (1)}$$

$$\sigma = \frac{A_1 E_1 (\varepsilon_I + \varepsilon_R)}{2A} + \frac{A_2 E_2 \varepsilon_T}{2A} \quad \text{Formula (2)}$$

In the formulas, $A_1$ is the cross-sectional area of the solid incident rod; $A_2$ is the cross-sectional area of the transmission rod; $E_1$ is the elastic modulus of the solid incident rod; $E_2$ is the elastic modulus of the transmission rod; $C_1$ is the longitudinal wave velocity of the solid incident rod; $C_2$ is the longitudinal wave velocity of the transmission rod; $\varepsilon_1$ is the incident pulse; $\varepsilon_T$ is the transmission pulse; $\varepsilon_R$ is the reflection pulse; A is the cross-sectional area of the rock-like material specimen 12; L is the length of the rock-like material specimen 12; $\sigma$ is a stress of the rock-like material specimen 12; $\varepsilon$ is a strain of the rock-like material specimen 12.

In step S60, before the stress wave data are acquired, data zeroing is performed. After the zeroing, the data are acquired. The transmission rod 9 may be a solid transmission rod or a hollow transmission rod. When the transmission rod is a hollow transmission rod, since the wave impedance of the rock is greater than that of the hollow transmission rod, reflected tensile waves are formed at a free surface of the rock-like material specimen 12, such that the rock-like material specimen 12 generates spalling destruction, and the spalling strength is obtained through the test. If the transmission rod is a solid transmission rod, the dynamic stress resistance is obtained through the test.

The spalling strength of the rock-like specimen is tested by utilizing the spalling damage to the rock mass caused by reflected tensile waves generated by mismatch of the wave impedance. The method is implemented through the mismatch of the wave impedance. A specific implementation is as follows: The calculation formula of the wave impedance is $\rho c$, where $\rho$ is the density of a medium, and c is the propagation velocity of stress waves in a medium. Since the wave impedance $\rho_{rock} c_{rock}$ of the rock-like material specimen is greater than the wave impedance $\rho_{air} c_{air}$ of air in the cavity of the hollow rod, reflected tensile waves are formed on a surface of the rock-like material specimen, resulting in the spalling destruction of the rock-like material specimen 12.

$P_{rock}$ is the medium density of the rock-like material specimen; $c_{rock}$ is the propagation velocity of the stress waves in the rock-like material specimen; $\rho_{air}$ is the density of the air in the cavity of the hollow rod; and $c_{air}$ is the propagation velocity of the stress waves in the air in the cavity of the hollow rod.

Preferably, in step S10, the T-shaped mold and the wire transferring hole 1 are coaxial; one end portion of the T-shaped mold has the same size as the first end portion of the solid incident rod 7. The body of the T-shaped mold has the same size as the charging hole 5, such that the explosive can be conveniently placed after molding. The charging hole 5 is communicated with the wire transferring hole in the hole packer 2, such that the leg wire for detonating the explosive can be conveniently output from the wire transferring hole. The charging hole 5 and the wire transferring hole 1 are coaxial.

Preferably, in step S60, when the transmission rod 9 is a hollow rod, a spalling strength is obtained by test; when the transmission rod 9 is a solid rod, a dynamic stress resistance is obtained by test.

According to the apparatus and the method, the impact waves and the gas expansion waves generated by the explosion of the explosive act on surrounding media. After the impact waves and the gas expansion waves are transmitted into a rod through the media, the rock-like material specimen 12 is destroyed under the interaction between the solid incident rod 7 and the transmission rod 9. The apparatus has three main functions: First, the apparatus can apply a confining pressure to the rock-like material specimen. Second, the apparatus can generate an explosion pressure load to apply a dynamic load to the rock-like material specimen. Third, the apparatus can test the stress resistance and strain resistance of the combined dynamic-static loading of the rock-like material specimen. When a solid rod is adopted for the transmission rod, the stress resistance of the combined dynamic-static loading is tested. When a hollow rod is adopted for the transmission rod, the strain spalling resistance of the combined dynamic-static loading is tested.

According to the apparatus and the method of the above embodiments, after the explosive explodes in the rock mass in actual blasting engineering, the effects of the impact waves and the gas expansion waves on the surrounding media are considered, and combined dynamic-static loading conditions where a deep rock mass is positioned are considered. The reflected tensile waves are generated by the mismatch of the wave impedance will cause spalling destruction on the rock mass to test the spalling strength of the rock mass. Meanwhile, when the explosive explodes, a loading velocity with higher strength can be achieved. Due to these factors, the apparatus and the method of the embodiment can acquire combined dynamic-static loading strength data of a rock that meets the engineering requirements.

What is claimed is:

1. An apparatus for testing combined dynamic-static loading strength of a rock-like material, comprising an explosion load loading device, a static load loading device, and a stress wave rod transferring device, wherein the explosion load loading device is connected with one end of the stress wave rod transferring device; the stress wave rod transferring device is connected with a rock-like material specimen; the stress wave rod transferring device is connected with the static load loading device;

the explosion load loading device comprises a hole packer provided with a wire transferring hole, an explosion load loader, a rock-like material layer, a charging hole, and a sealing cover, wherein one end of the hole packer is fixedly connected with one end of the explosion load loader; an inner cavity of the explosion load loader is filled with the rock-like material layer; the charging hole is provided in the rock-like material layer; one end of the charging hole is communicated with the wire transferring hole; the charging hole is filled with an explosive; the sealing cover is fixedly connected with the other end of the explosion load loader;

the stress wave rod transferring device comprises a solid incident rod and a transmission rod; one end of the solid incident rod passes through the sealing cover and is opposite to the charging hole; the other end of the solid incident rod is connected with the rock-like material specimen; one end of the transmission rod is connected with the rock-like material specimen; the solid incident rod and the transmission rod are positioned on two sides of the rock-like material specimen; and the explosion load loader is filled with the rock-like material layer; a T-shaped mold is placed in a filling process; after the rock-like material layer is molded, the T-shaped mold is removed to form the charging hole and a port; a first end portion of the solid incident rod close to the charging hole is cylindrical, and the first end portion fits the port.

2. The apparatus for testing the combined dynamic-static loading strength of the rock-like material according to claim 1, wherein a wave-absorbing plate is provided on an inner wall of the explosion load loader.

3. The apparatus for testing the combined dynamic-static loading strength of the rock-like material according to claim 1, wherein a truncated cone-shaped connecting portion is provided between the first end portion and a body of the solid incident rod; a diameter of the truncated cone-shaped connecting portion gradually increases towards a direction of the charging hole.

4. The apparatus for testing the combined dynamic-static loading strength of the rock-like material according to claim 1, wherein the transmission rod is a hollow rod or a solid rod.

5. The apparatus for testing the combined dynamic-static loading strength of the rock-like material according to claim 1, wherein the static load loading device comprises a confining pressure loader, an axial pressure carrier, and an axial pressure loader, wherein the confining pressure loader comprises a front loader with a sound emission wire transferring hole, a rear loader with a sound emission wire transferring hole, an upper loader with a sound emission wire transferring hole, and a lower loader with a sound emission wire transferring hole; the front loader is positioned at a front portion of the rock-like material specimen; the rear loader is positioned at a rear portion of the rock-like material specimen; the upper loader is positioned at an upper portion of the rock-like material specimen; the lower loader is positioned at a lower portion of the rock-like material specimen; the sound emission wire transferring hole of the front loader, the sound emission wire transferring hole of the rear loader, the sound emission wire transferring hole of the upper loader and the sound emission wire transferring hole of the lower loader all face the rock-like material specimen; and one end of the axial pressure carrier is connected with the transmission rod; and the axial pressure loader is connected with the other end of the axial pressure carrier.

6. A method for testing combined dynamic-static loading strength of a rock-like material using the apparatus according to claim 5, comprising:

S10, molding a filling material: connecting the hole packer with one end of the explosion load loader in a threaded manner, filling the explosion load loader with the rock-like material layer, and placing the T-shaped mold during the filling process, wherein one end portion of the T-shaped mold has a same size as the first end portion of the solid incident rod;

S20, charging: after the rock-like material layer is molded, removing the T-shaped mold to form the charging hole and the port, mounting and binding an electronic detonator in the explosive, threading a leg wire connected to the electronic detonator through the wire transferring hole, and placing the explosive in the charging hole;

S30, connecting devices: connecting the explosion load loader with the sealing cover; placing the first end portion of the solid incident rod into the port of an inner cavity of the rock-like material layer, wherein the first end portion fits the port; sequentially connecting the rock-like material specimen with the solid incident rod, connecting the transmission rod with the rock-like material specimen, connecting the transmission rod with the axial pressure carrier, and connecting the axial pressure carrier with the axial pressure loader; placing the front loader at the front portion of the rock-like material specimen, placing the rear loader at the rear portion of the rock-like material specimen, placing the upper loader at the upper portion of the rock-like material specimen, and placing the lower loader at the lower portion of the rock-like material specimen; mounting a sound emission probe on the rock-like material specimen, and outputting wires of the sound emission probe through the sound emission wire transferring hole of the front loader, the sound emission wire transferring hole of the rear loader, the sound emission wire transferring hole of the upper loader, and the sound emission wire transferring hole of the lower loader; pasting super-dynamic strain gauges at middle portions of the solid incident rod and the transmission rod;

S40, loading a static load: applying an axial pressure load to the transmission rod through the axial pressure loader; sequentially transferring the axial pressure load to the rock-like material specimen, the solid incident rod and the rock-like material layer through the transmission rod, and compacting the rock-like material layer under an action of the axial pressure load; applying different lateral pressure loads to the rock-like material specimen through the front loader, the rear loader, the upper loader, and the lower loader of the confining pressure loader;

S50, loading a dynamic load: detonating the explosive in the charging hole through the leg wire in the wire transferring hole, wherein impact waves and gas expansion waves generated by an explosion of the explosive push the solid incident rod to act on the rock-like material specimen, such that a combined dynamic-static loading is achieved on the rock-like material specimen; and S60, acquiring stress wave data: during the loading of the dynamic load, acquiring data in the super-dynamic strain gauges on the solid incident rod and the transmission rod.

7. The method for testing the combined dynamic-static loading strength of the rock-like material according to claim 6, wherein in step S10, the T-shaped mold and the wire transferring hole are coaxial, and a body of the T-shaped mold has a same size as the charging hole; the charging hole is communicated with the wire transferring hole in the hole packer.

8. The method for testing the combined dynamic-static loading strength of the rock-like material according to claim 6, wherein in step S60, when the transmission rod is a hollow rod, a spalling strength is obtained by a test; when the transmission rod is a solid rod, a dynamic stress resistance is obtained by a test.

* * * * *